United States Patent
Mijers

(10) Patent No.: US 11,560,953 B2
(45) Date of Patent: Jan. 24, 2023

(54) ANTI-FREE-FLOW VALVE

(71) Applicant: Illinois Tool Works Inc., Glenview, IL (US)

(72) Inventor: Jan Willem Marinus Mijers, Heemstede (NE)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 17/332,035

(22) Filed: May 27, 2021

(65) Prior Publication Data

US 2021/0404562 A1    Dec. 30, 2021

Related U.S. Application Data

(60) Provisional application No. 63/045,988, filed on Jun. 30, 2020.

(51) Int. Cl.
| | | |
|---|---|---|
| *F16K 15/18* | (2006.01) | |
| *F16K 7/12* | (2006.01) | |
| *F16K 31/60* | (2006.01) | |

(52) U.S. Cl.
CPC ............... *F16K 7/12* (2013.01); *F16K 15/18* (2013.01); *F16K 15/1825* (2021.08); *F16K 31/607* (2013.01)

(58) Field of Classification Search
CPC .... F16K 15/144; F16K 15/145; F16K 15/147; F16K 15/1471; F16K 15/18; F16K 15/1825; F16K 15/1845; F16K 7/02; F16K 7/04; A61M 2025/0075; A61M 2039/0646; A61M 39/2433; A61M 39/24; A61M 2039/246; A61M 2039/2426
See application file for complete search history.

(56) References Cited

U.S. PATENT DOCUMENTS

| | | | | |
|---|---|---|---|---|
| 2,755,060 A | * | 7/1956 | Raymond | ................. F16K 7/00 |
| | | | | 137/847 |
| 3,762,443 A | | 10/1973 | Sorenson | |
| 3,965,925 A | * | 6/1976 | Gooch | ...................... F16K 7/06 |
| | | | | 137/451 |
| 4,057,177 A | | 11/1977 | Laauwe | |
| 4,314,658 A | | 2/1982 | Laauwe | |

(Continued)

FOREIGN PATENT DOCUMENTS

WO    2014046271 A1    3/2014

OTHER PUBLICATIONS

Extended European Search Report dated Nov. 15, 2021 for corresponding Application No. 21181723.4 (7 pages).

*Primary Examiner* — Hailey K. Do
(74) *Attorney, Agent, or Firm* — The Small Patent Law Group LLC; Philip S. Hof

(57) ABSTRACT

An anti-free-flow valve includes a tube and a membrane. The tube extends from a first end of the tube to a second end of the tube. The tube defines a hollow cavity. The membrane is attached to an interior surface of the tube and extends across the hollow cavity to obstruct fluid flow through the hollow cavity. The membrane is spaced apart from the first and second ends of the tube. The membrane defines a slit therethrough that is configured to transition from a closed state that restricts fluid flow to an open state that permits fluid flow through the slit responsive to compression or expansion of the tube proximate to the membrane.

19 Claims, 5 Drawing Sheets

(56) References Cited

U.S. PATENT DOCUMENTS

| | | | | |
|---|---|---|---|---|
| 4,968,294 A | * | 11/1990 | Salama | A61F 5/453 |
| | | | | 128/DIG. 25 |
| 5,092,561 A | * | 3/1992 | Moriuchi | B29C 39/028 |
| | | | | 251/117 |
| 5,147,333 A | | 9/1992 | Raines | |
| 5,297,777 A | | 3/1994 | Yie | |
| 5,396,925 A | * | 3/1995 | Poli | F16K 17/18 |
| | | | | 137/493 |
| 5,707,357 A | * | 1/1998 | Mikhail | A61M 25/0017 |
| | | | | 604/167.03 |
| 5,800,339 A | | 9/1998 | Salama | |
| 6,726,063 B2 | | 4/2004 | Stull et al. | |
| 7,008,372 B2 | * | 3/2006 | Chaussy | A61F 2/82 |
| | | | | 604/246 |
| 7,037,303 B2 | * | 5/2006 | Beaufore | A61M 25/04 |
| | | | | 604/323 |
| 9,097,361 B1 | * | 8/2015 | Ratner | F16K 31/0672 |
| 2004/0082923 A1 | * | 4/2004 | Field | A61M 39/0613 |
| | | | | 251/340 |
| 2005/0242204 A1 | | 11/2005 | Ness et al. | |
| 2017/0156525 A1 | * | 6/2017 | Guy | B65D 47/2031 |
| 2020/0197683 A1 | * | 6/2020 | Muse | A61M 39/24 |

\* cited by examiner

ANTI-FREE-FLOW VALVE

CROSS-REFERENCE TO RELATED APPLICATIONS

This application claims priority benefit to U.S. Provisional Application No. 63/045,988, which was filed on 30 Jun. 2020, and the entire disclosure of which is incorporated herein by reference.

FIELD

The subject matter of the present application relates to controlling the flow of fluids through tubes.

BACKGROUND

Feeding sets can be used for enteral applications, and infusion sets can be used for parenteral applications. Enteral applications include using an enteral pump to administer nutrition (e.g., food, formula, medication, and the like) to a patient if the patient is unable to accept the nutrition without assistance. Parenteral applications include providing intravenous (IV) solutions to the patient to ensure adequate hydration and to provide needed nutrients, minerals, and/or medication. Often, the feeding or infusion set is placed in a free standing arrangement in which gravity causes the flow of formula or solution into the patient. The rate at which the formula or solution enters the patient can be generally controlled by various clamps, such as roller clamps.

In many applications, it is necessary to precisely control of the amount of solution or formula which enters the patient. A regulating device, such as an infusion pump, can be placed along the feeding or infusion set to control the rate at which the nutrition or solution is supplied to the patient. To avoid interference with the functioning of the regulating device, any clamps or valves that are present along the length of the tube may be opened to the fullest extent, with the expectation that the pump or other regulating device will control the flow through the tubing. However, emergencies and other distractions may prevent the medical personnel from properly setting up the feeding or infusion set with the automated regulating device. Furthermore, the feeding or infusion sets may be inadvertently dislodged from the regulating device during operation. In the unfortunate event that the regulating device is not properly connected to the feeding or infusion set due to negligent setup or unintentional dislodgement, an excessive flow of fluid may develop through the set under the force of gravity, which is a condition known as free-flow. During the free-flow condition, the patient may receive an excessive amount of nutrition, medication, and/or solution within a relatively short time period, which can be particularly dangerous if the medication is potent and/or the patient's body is not physically strong enough to adjust to the large inflow of nutrition (e.g., formula) or solution.

BRIEF DESCRIPTION

In one or more embodiments, an anti-free-flow valve is provided that includes a tube and a membrane. The tube extends from a first end of the tube to a second end of the tube. The tube defines a hollow cavity. The membrane is attached to an interior surface of the tube and extends across the hollow cavity to obstruct fluid flow through the hollow cavity. The membrane is spaced apart from the first and second ends of the tube. The membrane defines a slit therethrough that is configured to transition from a closed state that restricts fluid flow to an open state that permits fluid flow through the slit responsive to compression or expansion of the tube proximate to the membrane.

In one or more embodiments, an anti-free-flow valve is provided that includes a tube, a membrane, and first and second engagement tabs. The tube defines a hollow cavity. The membrane is attached to an interior surface of the tube and extends across the hollow cavity to obstruct fluid flow through the hollow cavity. The membrane defines a slit through a thickness of the membrane. The first and second engagement tabs are attached to an exterior surface of the tube proximate to a location of the membrane. The first and second engagement tabs radially extend from the tube in opposite directions and are configured to be manipulated to compress or expand the tube to selectively transition the slit from a closed state that restricts fluid flow to an open state that permits fluid flow through the slit.

In one or more embodiments, an anti-free-flow valve is provided that includes a tube, a membrane, and first and second engagement tabs. The tube defines a hollow cavity. The membrane is attached to an interior surface of the tube and extends across the hollow cavity to obstruct fluid flow through the hollow cavity. The membrane defines a linear slit through a thickness of the membrane. The first and second engagement tabs are attached to an exterior surface of the tube proximate to a location of the membrane. The first and second engagement tabs radially extend from the tube in opposite directions along a tab axis that is parallel to the slit. The first and second engagement tabs are configured to be squeezed towards each other to compress the tube along the tab axis at the membrane which transitions the slit to an open state that permits fluid flow through the slit. Releasing the first and second engagement tabs causes the tube to decompress and the slit on the membrane to resiliently return to a closed state that restricts fluid flow.

BRIEF DESCRIPTION OF THE DRAWINGS

The inventive subject matter will now be illustrated with reference to the following figures, in which.

DETAILED DESCRIPTION

Figure 1:
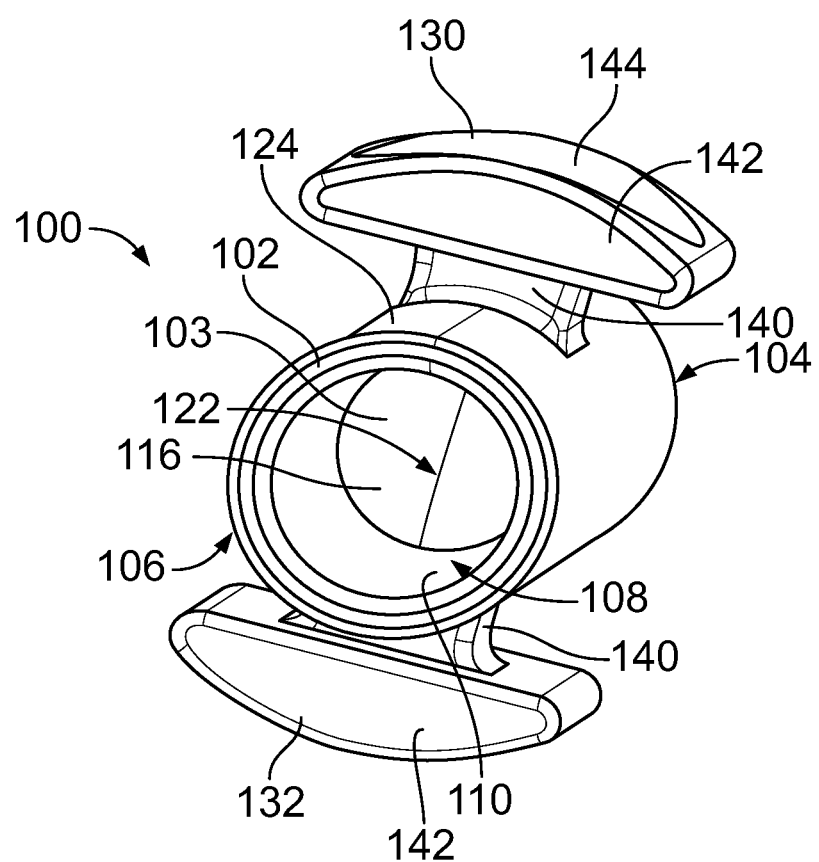
FIG. 1 illustrates an anti-free-flow valve according to an embodiment of the present disclosure.

Embodiments set forth herein include a valve that is integrated with a tube. The valve has a membrane within the tube that obstructs flow of liquid or semi-liquid contents of the tube. The valve is configured to prevent free-flow of the contents, and for this reason is referred to herein as an anti-free-flow valve. The membrane of the valve can transition between a closed state and an open state. In the closed state, the membrane prevents the tube contents from passing beyond the membrane. In the open state, the membrane provides an opening that permits the contents to pass beyond the membrane via the opening. The membrane is biased towards to the closed state such that the membrane defaults to blocking the passage of the tube contents. The valve is designed to enable the membrane to transition to the open state based on mechanical manipulation of the tube itself. For example, compression and/or expansion of the tube may temporarily change the shape of the membrane which exposes or enlarges the opening to permit the contents to pass through the opening. The compressive forces can be applied by squeezing the tube, such as between two fingers or between prongs of a tool. The expansive forces can be applied by pulling two, circumferentially-opposite portions of the tube away from each other to radially stretch the tube. The pinching or pulling of the tube that actuates the valve can be performed manually by a human operator, semi-automatically by a human-controlled automated instrument or robot, or fully automatically. Upon releasing the tube or at least removing the compressive or expansive forces on the tube, the membrane resiliently returns to the closed state. The valve may also be configured to automatically open in response to the pressure exerted by the contents on the membrane exceeding a designated threshold force, and return to the closed state once the pressure drops below the designated threshold force.

The anti-free-flow valve can be used for various applications. In non-limiting examples, the valve can be integrated into the tubes of infusion (e.g., parenteral) sets and feeding (e.g., enteral) sets. When used in the infusion or IV set, the valve can be actuated to open the membrane in order to prime for pre-filling, then the valve is released. Once released, the valve returns to the closed state to prevent free-flow of the contents through the tube, preventing the patient from receiving an excessive amount or rate of the tube contents. When used in conjunction with a pump or other regulating device that controls the flow of the contents through the tube to the patient, the valve does not interfere with the operations of the pump to supply the contents at a designated rate or amount. For example, the pump may exert sufficient positive or negative pressure within the tube to cause the membrane to open without requiring active compression or expansion of the tube. The anti-free-flow valve described in the embodiments herein can also be utilized in other applications that require metering the flow of fluids and fluid-like contents through tubes, such as other types of medical applications, laboratory applications, industrial applications, and the like.

In at least one embodiment of the present disclosure, an anti-free-flow valve includes a tube and a membrane. The tube defines a hollow cavity. The membrane is attached to an interior surface of the tube and extends across the hollow cavity to obstruct fluid flow through the hollow cavity. The membrane is medially-located within the tube such that the membrane is spaced apart from ends of the tube. The membrane defines a narrow opening, referred to as a slit, therethrough. The slit may represent the only possible flow path across or beyond the membrane, such that when the slit is closed or sealed the membrane blocks fluid flow through the hollow cavity of the tube. The tube and the membrane are composed of one or more elastomeric materials which enable the tube and the membrane to deform and resiliently return to the pre-deformed shapes upon removal of the mechanical stimulus. Compression or expansion of the tube may cause the membrane flaps that define the slit to separate, establishing an opening through the membrane that permits fluid flow through the membrane.

One or more technical effects of the valve according to the embodiments described herein include increasing the safety and accuracy of metered flow operations, such as medical infusion sets and feeding sets, by preventing free-flow of the fluid contents through the tube. Anther technical effect is reduced complexity to manufacture and to operate relative to at least some known valves used for similar functions, as the known valves typically include multiple discrete rigid hardware pieces to which the tube connects. The anti-free-flow valve disclosed herein is integrated into the tube and may lack rigid hardware and tube coupling members. As described herein, the valve may have few components other than the membrane within the tube, which may simplify the manufacturing process. Furthermore, the valve may be manually actuated by simply compressing or expanding the tube, and thus does not require special tools or extended time to operate. Yet another technical effect that is related to the reduced complexity is reduced cost. The membrane could be integrally manufactured with the tube, even using the same elastomeric material composition. The relatively few components of the valve and the common materials can result in low manufacturing costs.

In the following description and claims, relative or spatial terms such as "front," "back," "side," "top," "bottom," "lateral," "longitudinal," and the like are only used to distinguish the referenced elements or features with respect to one another and make the language more readily understandable. The terms do not necessarily require particular positions, sizes, or orientations relative to the surrounding environment. Moreover, in the following description and claims, the terms "first," "second," and "third," etc. may be used as labels to distinguish similar elements (e.g., first and second side walls) and are not intended to impose numerical requirements on their objects.

Figure 2:
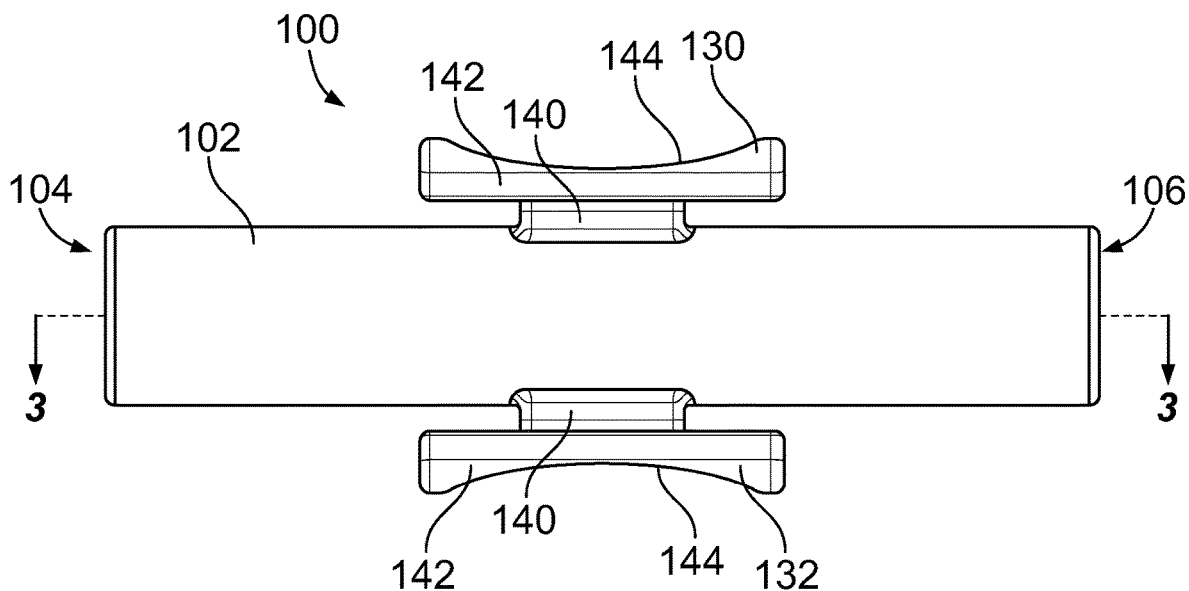
FIG. 2 illustrates a side view of the anti-free-flow valve of FIG. 1.

FIG. 1 illustrates an anti-free-flow valve 100 according to an embodiment of the present disclosure. FIG. 2 illustrates a side view of the anti-free-flow valve 100 of FIG. 1. The valve 100 includes a tube 102 and a membrane 103.

The tube 102 extends from a first end 104 to a second end 106 that is opposite the first end 104. The tube 102 has a short length between the first and second ends 104, 106 in FIGS. 1 and 2, but the tube 102 can be longer than the illustrated segment length. For example, the tube 102 may have a length that is several meters. The tube 102 is hollow and defines a cavity 108 (e.g., a hollow cavity) that extends the length of the tube 102 from the first end 104 to the second end 106. The tube 102 is flexible and compressible. For example, the tube 102 may be composed of one or more elastomeric materials, such as silicone rubber, polyethylene, polypropylene, and other thermoplastic elastomers. In a non-limiting embodiment, the material of the tube 102 may have a shore hardness that is in a range no less than 50 Shore A and no greater than 80 Shore A, such as no less than 60 Shore A and no greater than 70 Shore A. The specified durometer range may enable the tube 102 to have effective properties for the various applications of the valve 100. The tube 102 may be molded into the hollow cylindrical shape. The inner diameter of the tube 102 (e.g., the diameter of the cavity 108) may be selected based on application-specific considerations, such as the required flow rate of the contents that flow through the tube 102, the viscosity of the contents, the size of any solid or semi-solid constituents within the contents, such as constituents within a feeding formula, the size of components that connect to the ends 104, 106 of the tube 102 in an assembly, and the like. In a non-limiting embodiment, the inner diameter may be between 1 mm and 10 mm, such as between 3 mm and 8 mm, and more specifically about 5 mm.

Figure 3:
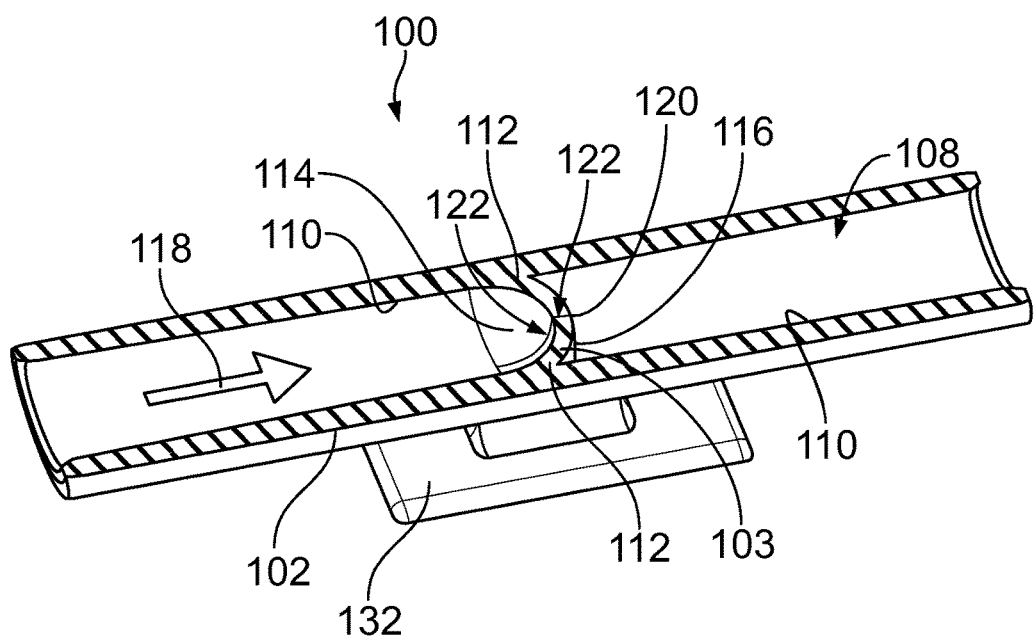
FIG. 3 shows a cross-sectional view of the anti-free-flow valve taken along the line 3-3 in FIG. 2.

Reference is additionally made to FIG. 3, which shows a cross-sectional view of the anti-free-flow valve 100 taken along the line 3-3 in FIG. 2. The membrane 103 is disposed within the cavity 108 and is spaced apart from the ends 104, 106 of the tube. The membrane 103 is secured in a fixed position within the cavity 108. The membrane 103 is attached to an interior surface 110 of the tube 102 that defines the cavity 108. In at least one embodiment, the membrane 103 is continuously, uninterruptedly sealed to the tube 102 along the full circumference of the interior surface 110 such that there is no flow or leak paths between a perimeter edge 112 of the membrane 103 and the interior surface 110. The membrane 103 has a thickness that extends from a first face 114 to a second face 116 that is opposite the first face 114. In an embodiment in which the contents of the tube are controlled to flow or move in the direction indicated by arrow 118 in FIG. 3, the first face 114 faces upstream and the second face 116 faces downstream. The thickness of the membrane 103 may be similar to the thickness of the tube 102. The membrane thickness may be in the range between 0.5 mm and 2 mm, such as about 1 mm.

In an embodiment, the membrane 103 is concave such that a radial center point 120 of the membrane 103 is axially disposed between the perimeter edge 112 of the membrane 103 and the second end 106 of the tube 102. Stated differently, the membrane 103 bows towards the second end 106, and the center point 120 is the closest portion of the membrane 103 to the second end 106. In an embodiment, the concave curvature is three-dimensional, such that the membrane 103 is semi-spherical.

The membrane 103 may be integrally connected to the tube 102. For example, the perimeter edge 112 of the membrane 103 may be seamlessly attached to the interior surface 110 of the tube 102. The tube 102 and the membrane 103 may define a unitary, one-piece, monolithic structure. For example, the membrane 103 may be formed with the tube 102 during a common manufacturing process. The membrane 103 therefore may be composed of the same elastomeric material as the tube 102. In an alternative embodiment, the membrane 103 may be separately formed from the tube 102 and subsequently secured to the interior surface 110 via an adhesive, a heat application, or the like.

The membrane 103 defines a slit 122 that extends through the full thickness of the membrane 103 between the first and second faces 114, 116. The slit 122 is a narrow slice or cut which may be formed by penetrating the membrane 103 with a fine cutting instrument, such as a blade. In the illustrated embodiment, the slit 122 is linear. The slit 122 may extend through the center point 122 of the membrane 103. The linear slit 122 may extend the full arc length from the perimeter edge 112 of the membrane 103 through the center point 122 to the opposite location of the perimeter edge 112. In such an embodiment, the slit 122 bifurcates the membrane 103 into two halves or flaps. Alternatively, the slit 122 may have a shorter length such that the two segments of the membrane 103 on either side of the slit 122 are integrally connected at the ends of the slit 122.

When the membrane 103 is free of interior fluid pressures within the cavity 108 and free of mechanical forces exerted on the exterior of the tube 102, the edges of the membrane 103 that define the slit 122 press up against each other. The edges of the membrane 103 pressing against each other close or seal the slit 122 to restrict (e.g., block) fluid flow through the slit 122. This state of the membrane 103 is referred to as a closed state. The membrane 103 is biased towards the closed state, so the membrane 103 is referred to as self-sealing.

As shown in FIG. 3, when fluid contents within the tube 102 flow in the direction 118, due to gravity for example, the contents abut against the concave membrane 103 in the closed state. The membrane 103 blocks flow of the contents beyond the membrane 103 unless or until sufficient force is applied to cause the membrane 103 to transition to an open state which permits the contents to pass through the slit 122 beyond the membrane 103. The curved shape of the membrane 103 channels or funnels the contents to the slit 122 at the center point 120. In one example, if a pump connected to the tube 102 exerts sufficient positive or negative pressure based on the position of the pump, the pressure may cause the membrane 103 to deform from the closed state to the open state. For example, the edges that define the slit 122 may pull apart from each other which enlarges and deforms the slit 122 to provide a void through the membrane 103. The contents therefore can be pushed or sucked through the slit 122 if the internal pressure is sufficient to overcome the natural resiliency of the membrane 103 to seal the slip 122.

The membrane 103 can also transition to the open state by compression or expansion of the tube 102 proximate to the membrane 103, as described herein. The compression or expansion proximate to the membrane 103 refers to forces exerted on the tube 102 that are close enough to the membrane 103 such that the deformation of the tube 102 causes the membrane 103 within the tube 102 to deform. The forces may be exerted on the tube 102 at the location of the membrane 103 or within a designated proximity of the membrane 103, which may depend on various parameters such as the internal diameter of the tube 102 and the material properties of the tube 102.

Referring to FIGS. 1 and 2, the valve 100 in at least one embodiment includes a first engagement tab 130 and a second engagement tab 132 that can be used to compress and/or expand the tube 102. The engagement tabs 130, 132 are coupled to an exterior surface 124 of the tube 102 and radially extend from the tube 102 in opposite directions from each other. For example, the engagement tabs 130, 132 may be coupled to the tube 102 at locations that are 180 degrees apart in the circumferential dimension but at the same position along the length of the tube 102. The engagement tabs 130, 132 are located at or proximate to the location of the membrane 103. The engagement tabs 130, 132 are fixed to the tube 102 and configured to be manipulated to selectively compress or expand the tube 102 to transition the membrane 103 to the open state. The tabs 130, 132 may be sized and shaped to accommodate manual manipulation, such as by two fingers pressing the engagement tabs 130, 132 together or two sets of fingers gripping the engagement tabs 130, 132 to pull the tabs 130, 132 in opposite directions. The tabs 130, 132 may also accommodate manipulation by instruments, such as tools or robots that engage the tabs 130, 132. In an embodiment, the engagement tabs 130, 132 may be integrally formed with the tube 102, such as formed during a common molding process with the tube 102. Alternatively, the engagement tabs 130, 132 may be discretely formed separate from the tube 102 and subsequently secured to the exterior surface 124 via adhesive, a heat treatment, a pressure treatment, or the like.

The engagement tabs 130, 132 in various embodiments can have different shapes and/or sizes. In the illustrated embodiment, the engagement tabs 130, 132 each have a trunk 140 and a cap 142. The trunk 140 is a base or post that attaches to the tube 102 and extends radially outward from the exterior surface 124. The cap 142 is mounted to the end of the trunk 140 such that the trunk 140 is between the tube 102 and the cap 142. The cap 142 has a broader size than the trunk 140 in the illustrated embodiment. For example, portions of the cap 142 extend beyond and overhang the trunk 140. The overhanging portions can be gripper or grasped by a user's fingers or an instrument to enable pulling the engagement tabs 130, 132 apart to expand the tube 102. The cap 142 has an outer surface 144 that faces away from the tube 102. The outer surface 144 is sufficiently broad to enable a user's finger or an instrument to press on the outer surface 144 to enable pushing the engagement tabs 130, 132 together to compress the tube 102. As shown in FIG. 2, the outer surface 144 is concave. The concave outer surface 144 can provide tactile guidance for the user when placing the user's fingers on the engagement tabs 130, 132.

Figure 4:
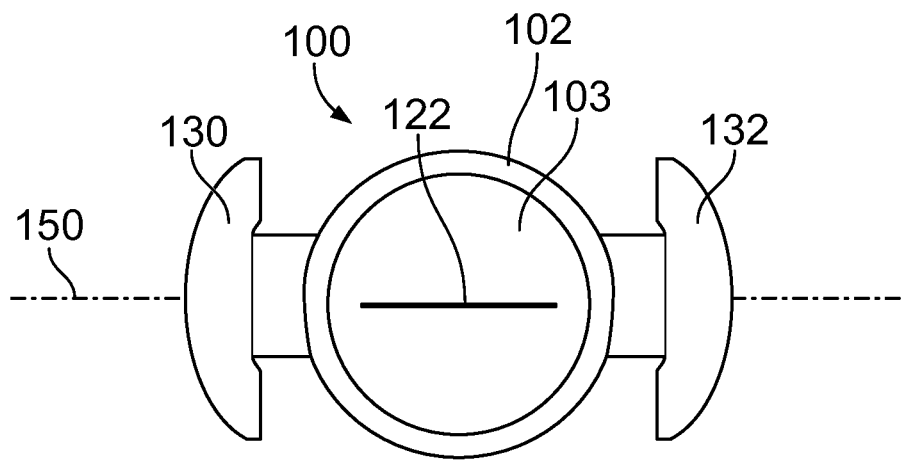
FIG. 4 is an end view of the anti-free-flow valve according to the embodiment shown in FIGS. 1-3 with the membrane in a closed state.
Figure 5:
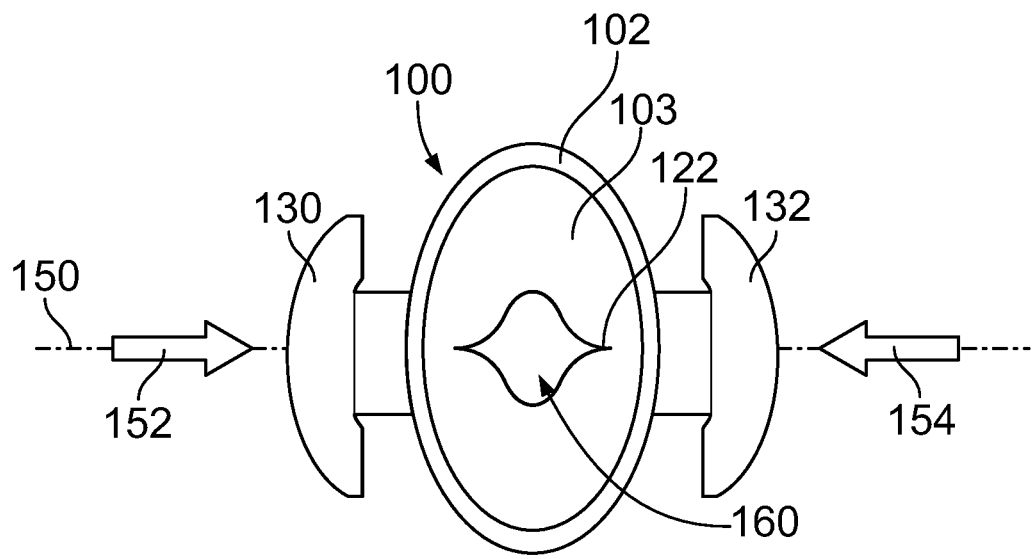
FIG. 5 is an end view of the anti-free-flow valve of FIGS. 1-4 with the membrane in an open state.

FIG. 4 is an end view of the anti-free-flow valve 100 according to the embodiment shown in FIGS. 1-3 with the membrane 103 in the closed state. FIG. 5 is an end view of the anti-free-flow valve 100 of FIGS. 1-4 with the membrane 103 in the open state. As shown in FIG. 4, the slit 122 is linear and centrally located on the membrane 103. The engagement tabs 130, 132 project from the tube 102 in opposite directions along a tab axis 150. The tab axis 150 is parallel to the slit 122. FIG. 4 shows the valve 100 in a default resting state. In the illustrated embodiment, the membrane 103 can be selectively transitioned to the open state by compressing the tube 102. As shown in FIG. 5, forces applied on the engagement tabs 130, 132 in the direction of arrows 152, 154, respectively, squeeze the engagement tabs 130, 132 towards each other. The engagement tabs 130, 132 compress the tube 102 along the tab axis 150. The compression of the tube 102 deforms the membrane 103, which causes the slit 122 to open and enlarge. The narrow slit 122 opens to define a passage 160 through the membrane 103. When in the open state, the fluid or semi-fluid contents of the tube 102 can pass beyond the membrane 103 through the passage 160. Upon removal or at least reduction of the forces in the directions 152, 154, the tube 102 and the membrane 103 resiliently return towards the inherent molded shapes thereof. The flaps of the membrane 103 move together and close or seal the slit 122 as the membrane decompresses. Thus, a user can selectively open or bypass the anti-free-flow valve 100 by squeezing the engagement tabs 130, 132 together, and can release the tabs 130, 132 to close the valve 100.

Figure 6:
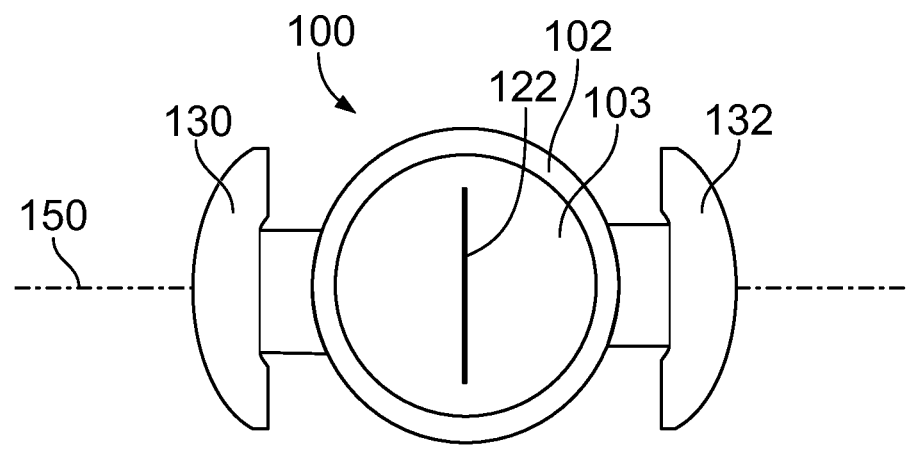
FIG. 6 is an end view of the anti-free-flow valve according to a second embodiment showing the membrane in the closed state.
Figure 7:
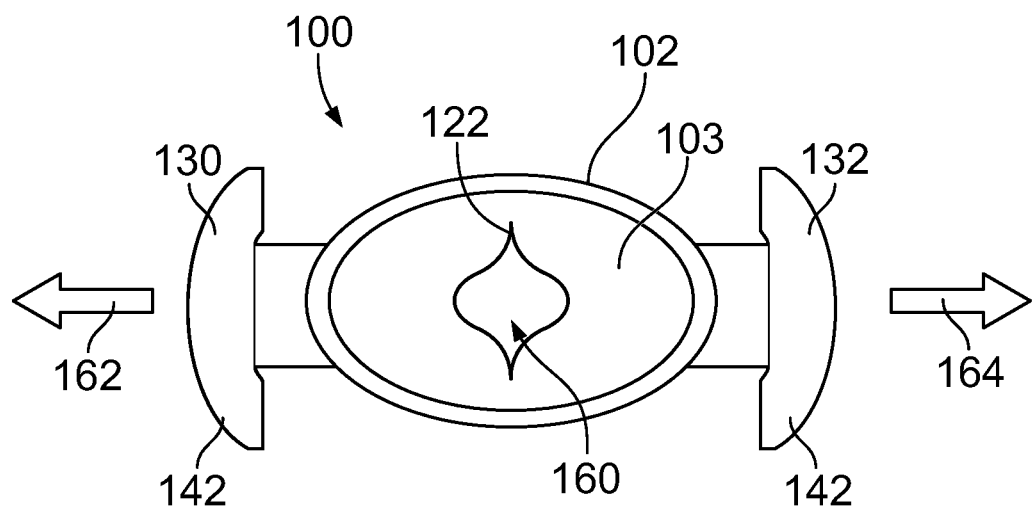
FIG. 7 is an end view of the anti-free-flow valve of FIG. 6 showing the membrane in the open state.

FIG. 6 is an end view of the anti-free-flow valve 100 according to a second embodiment showing the membrane 103 in the closed state. FIG. 7 is an end view of the anti-free-flow valve 100 of FIG. 6 showing the membrane 103 in the open state. The only difference between the illustrated embodiment and the first embodiment shown in FIGS. 1-5 is the orientation of the linear slit 122 relative to the positioning of the engagement tabs 130, 132. For example, the tab axis 150 defined by the engagement tabs 130, 132 is orthogonal to the orientation of the slit 122 in FIG. 6, instead of parallel as shown in FIG. 4. In the illustrated arrangement, the membrane 103 transitions from the closed state to the open state by expanding the tube 102 along the tab axis 150. The expansion can be achieved by pulling the engagement tabs 130, 132 apart from each other in the direction of arrows 162, 164. For example, the user may grip the engagement tabs 130, 132 at the overhanging portions of the caps 142. The expansion of the tube 102 deforms the membrane 103, which causes the slit 122 to open and enlarge to define the passage 160 through the membrane 103. The first embodiment shown in FIGS. 1-5 may represent a compression-actuated anti-free-flow valve 100, and the second embodiment shown in FIGS. 6 and 7 may be an expansion-actuated anti-free-flow valve 100.

Figure 8:
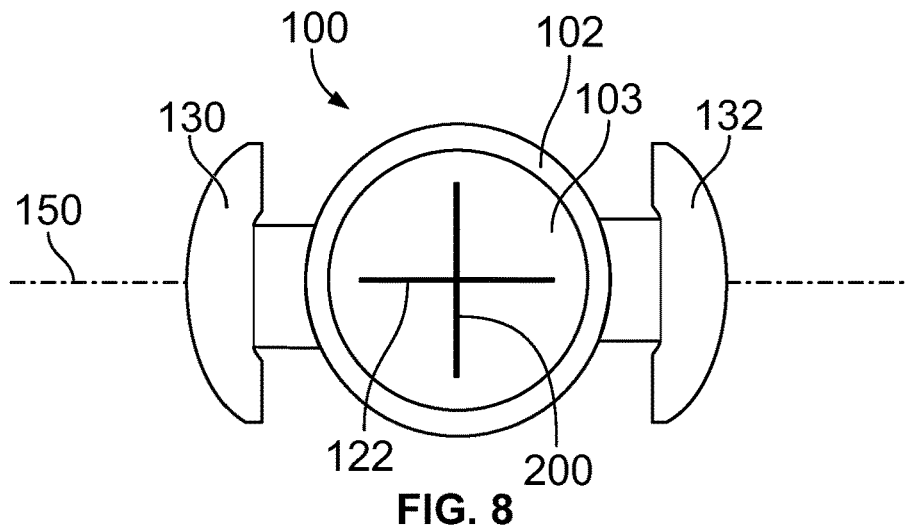
FIG. 8 is an end view of the anti-free-flow valve according to a third embodiment showing the membrane in the closed state.

FIG. 8 is an end view of the anti-free-flow valve 100 according to a third embodiment showing the membrane 103 in the closed state. The third embodiment may represent a hybrid of the first and second embodiments described above. For example, the membrane 103 in FIG. 8 has the (first) slit 122 and a second slit 200 therethrough. The two slits 122, 200 intersect. In an embodiment, each slit 122, 200 is linear and the slits 122, 200 are oriented orthogonal to each other to form an X-shaped incision in the membrane 103. The first slit 122 is parallel to the tab axis 150, and the second slit 200 is orthogonal to the tab axis 150. The anti-free-flow valve 100 is designed to selectively open based on either of tube compression via pressing the engagement tabs 130, 132 together or tube expansion via pulling the engagement tabs 130, 132 apart.

Figure 9:
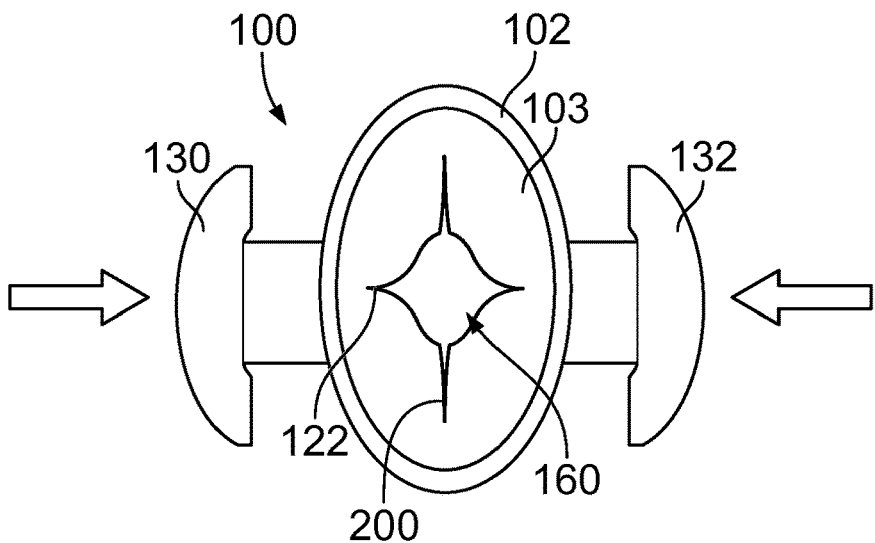
FIG. 9 is an end view of the anti-free-flow valve of FIG. 8 showing the membrane in a first open state.
Figure 10:
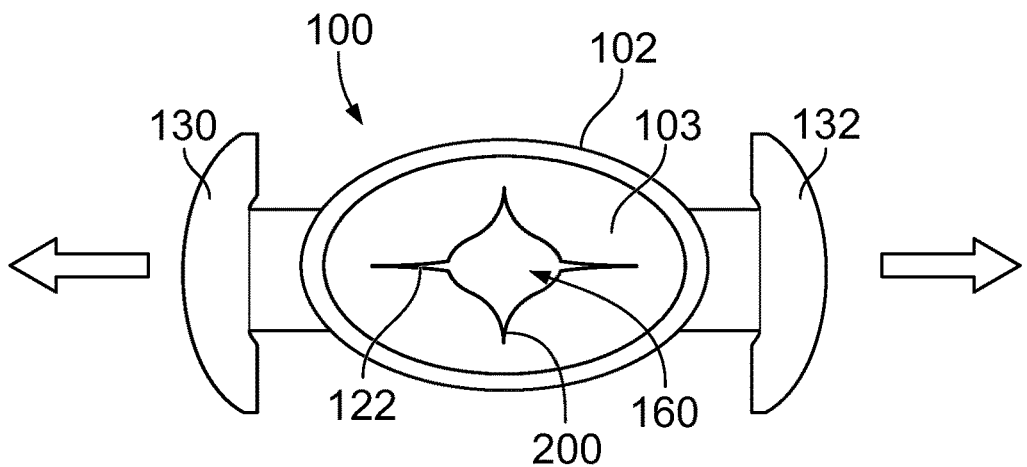
FIG. 10 is an end view of the anti-free-flow valve of FIG. 8 showing the membrane in a second open state.

FIG. 9 is an end view of the anti-free-flow valve 100 of FIG. 8 showing the membrane 103 in a first open state. FIG. 10 is an end view of the anti-free-flow valve 100 of FIG. 8 showing the membrane 103 in a second open state. In the first open state shown in FIG. 9, the engagement tabs 130, 132 are pressed together similar to the actuation shown in FIG. 5. The result is that the first slit 122 opens and enlarges to define the passage 160 that permits fluid flow through the membrane 103. The second slit 200 may open only slightly in the region proximate to the intersection with the first slit 122 because the compression of the tube 102 limits the spreading of the second slit 200. The second open state shown in FIG. 10 is essentially the inverse as the first open state. When the engagement tabs 130, 132 are pulled apart, similar to the actuation shown in FIG. 7, the second slit 200 opens and enlarges to define the passage 160 that permits fluid flow through the membrane 103. The first slit 122 may open only slightly in the region proximate to the intersection because the expansion of the tube 102 limits the spreading of the first slit 122. Thus, the hybrid anti-free-flow valve 100 shown in FIGS. 8-10 can be actuated from the closed state to the open state by either pulling or pressing the engagement tabs 130, 132, which provides flexibility for use in various different applications.

In an embodiment, an anti-free-flow valve is provided that includes a tube and a membrane. The tube extends from a first end of the tube to a second end of the tube. The tube defines a hollow cavity. The membrane is attached to an interior surface of the tube and extends across the hollow cavity to obstruct fluid flow through the hollow cavity. The membrane is spaced apart from the first and second ends of the tube. The membrane defines a slit therethrough that is configured to transition from a closed state that restricts fluid flow to an open state that permits fluid flow through the slit responsive to compression or expansion of the tube proximate to the membrane.

Optionally, the membrane is concave such that a center point of the membrane is axially disposed between a perimeter edge of the membrane and the second end of the tube. The membrane may be semi-spherical, and the slit extends through the center point of the membrane.

Optionally, the membrane is integrally connected to the tube to define a seamless monolithic structure. Optionally, the membrane is attached to the interior surface along an entire circumference of the tube such that the slit represents an only flow passageway with the hollow cavity across the membrane. Optionally, the slit is linear and the membrane is biased towards the closed state of the slit. Optionally, the tube and the membrane comprise an elastomeric material that has a shore hardness in a range no less than 50 Shore A and no greater than 80 Shore A. Optionally, the slit is a first slit, and the membrane also defines a second slit that intersects the first slit.

The anti-free-flow valve may also include a first engagement tab and a second engagement tab attached to an exterior surface of the tube proximate to a location of the membrane and radially extending from the tube in opposite directions. The first and second engagement tabs are configured to be manipulated to compress or expand the tube to selectively transition the slit to the open state. Each of the first and second engagement tabs may include a cap and a trunk disposed between the cap and the tube. The cap has a broader size than the trunk. An outer surface of the cap of each of the first and second engagement tabs radially faces away from the tube and defines a concave curve.

In an embodiment, an anti-free-flow valve is provided that includes a tube, a membrane, and first and second engagement tabs. The tube defines a hollow cavity. The membrane is attached to an interior surface of the tube and extends across the hollow cavity to obstruct fluid flow through the hollow cavity. The membrane defines a slit through a thickness of the membrane. The first and second engagement tabs are attached to an exterior surface of the tube proximate to a location of the membrane. The first and second engagement tabs radially extend from the tube in opposite directions and are configured to be manipulated to compress or expand the tube to selectively transition the slit from a closed state that restricts fluid flow to an open state that permits fluid flow through the slit.

Optionally, the slit is linear, and the first and second engagement tabs radially extend from the tube in opposite directions along a tab axis that is parallel to the slit. Compression of the tube by squeezing the first and second engagement tabs towards each other transitions the slit to the open state.

Optionally, the slit is linear, and the first and second engagement tabs radially extend from the tube in opposite directions along a tab axis that is orthogonal to the slit. Expansion of the tube by pulling the first and second engagement tabs away from each other transitions the slit to the open state. Optionally, the slit is a first slit, and the membrane also defines a second slit that is linear and oriented orthogonal to the first slit. Compression of the tube by squeezing the first and second engagement tabs towards each other transitions the second slit to the open state.

Optionally, the tube extends from a first end of the tube to a second end of the tube. The membrane is spaced apart from the first and second ends. Optionally, the membrane is integrally connected to the tube to define a seamless monolithic structure. Optionally, the membrane is concave such that a center point of the membrane is axially disposed between a perimeter edge of the membrane that is attached to the interior surface and an end of the tube.

Optionally, each of the first and second engagement tabs includes a cap and a trunk disposed between the cap and the tube. The cap has a broader size than the trunk.

In an embodiment, an anti-free-flow valve is provided that includes a tube, a membrane, and first and second engagement tabs. The tube defines a hollow cavity. The membrane is attached to an interior surface of the tube and extends across the hollow cavity to obstruct fluid flow through the hollow cavity. The membrane defines a linear slit through a thickness of the membrane. The first and second engagement tabs are attached to an exterior surface of the tube proximate to a location of the membrane. The first and second engagement tabs radially extend from the tube in opposite directions along a tab axis that is parallel to the slit. The first and second engagement tabs are configured to be squeezed towards each other to compress the tube along the tab axis at the membrane which transitions the slit to an open state that permits fluid flow through the slit. Releasing the first and second engagement tabs causes the tube to decompress and the slit on the membrane to resiliently return to a closed state that restricts fluid flow.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are example embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

What is claimed is:

1. An anti-free-flow valve comprising:
   a tube extending from a first end of the tube to a second end of the tube, the tube defining a hollow cavity,
   a membrane attached to an interior surface of the tube and extending across the hollow cavity to obstruct fluid flow through the hollow cavity, the membrane spaced apart from the first and second ends of the tube, wherein the membrane defines a slit therethrough that is configured to transition from a closed state that restricts fluid flow to an open state that permits fluid flow through the slit responsive to compression or expansion of the tube proximate to the membrane, wherein the membrane has a concave curved shape that extends to a center point of the membrane and the slit extends through the center point, the membrane oriented relative to a direction of the fluid flow through the tube such that the concave curved shape funnels the fluid flow towards the slit; and a first engagement tab and a second engagement tab attached to an exterior surface of the tube proximate to a location of the membrane and radially extending from the tube in opposite directions along a tab axis, wherein the slit of the membrane is configured to transition from the closed state to the open state in response to the first and second engagement tabs being pulled away from each other to expand the tube along the tab axis.

2. The anti-free-flow valve of claim 1, wherein the membrane is semi-spherical.

3. The anti-free-flow valve of claim 1, wherein the membrane is integrally connected to the tube to define a seamless monolithic structure.

4. The anti-free-flow valve of claim 1, wherein the slit is linear and the membrane is biased towards the closed state of the slit.

5. The anti-free-flow valve of claim 1, wherein the slit is a first slit and the membrane also defines a second slit that intersects the first slit.

6. The anti-free-flow valve of claim 1, wherein the tube and the membrane comprise an elastomeric material that has a shore hardness in a range no less than 50 Shore A and no greater than 80 Shore A.

7. The anti-free-flow valve of claim 1, wherein the membrane is attached to the interior surface along an entire circumference of the tube such that the slit represents an only flow passageway with the hollow cavity across the membrane.

8. The anti-free-flow valve of claim 1, wherein each of the first and second engagement tabs includes a cap and a trunk disposed between the cap and the tube, the cap having a broader size than the trunk.

9. The anti-free-flow valve of claim 8, wherein an outer surface of the cap of each of the first and second engagement tabs radially faces away from the tube and defines a concave curve.

10. The anti-free-flow valve of claim 1, wherein the slit is linear and the tab axis defined by the first and second engagement tabs is orthogonal to the slit.

11. The anti-free-flow valve of claim 10, wherein the tube is configured to resiliently retract in response to releasing the first and second engagement tabs, the retraction of the tube causing the slit of the membrane to transition from the open state to the closed state.

12. An anti-free-flow valve comprising:
a tube defining a hollow cavity;
a membrane attached to an interior surface of the tube and extending across the hollow cavity to obstruct fluid flow through the hollow cavity, wherein the membrane defines a slit through a thickness of the membrane, the slit being linear; and
first and second engagement tabs attached to an exterior surface of the tube proximate to a location of the membrane, wherein the first and second engagement tabs radially extend from the tube in opposite directions along a tab axis that is orthogonal to the slit, wherein the first and second engagement tabs are configured to be pulled away from each other to expand the tube along the tab axis and transition the slit from a closed state that restricts fluid flow to an open state that permits fluid flow through the slit.

13. The anti-free-flow valve of claim 12, wherein the slit is a first slit and the membrane also defines a second slit that is linear and oriented orthogonal to the first slit, wherein compression of the tube by squeezing the first and second engagement tabs towards each other transitions the second slit to the open state.

14. The anti-free-flow valve of claim 12, wherein the tube extends from a first end of the tube to a second end of the tube, and the membrane is spaced apart from the first and second ends.

15. The anti-free-flow valve of claim 12, wherein the membrane is integrally connected to the tube to define a seamless monolithic structure.

16. The anti-free-flow valve of claim 12, wherein each of the first and second engagement tabs includes a cap and a trunk disposed between the cap and the tube, the cap having a broader size than the trunk.

17. The anti-free-flow valve of claim 12, wherein the membrane is concave relative to a direction of the fluid flow through the tube such that concave curved surfaces of the membrane funnel the fluid flow towards the slit.

18. An anti-free-flow valve comprising:
a tube defining a hollow cavity;
a membrane attached to an interior surface of the tube and extending across the hollow cavity to obstruct fluid flow through the hollow cavity, wherein the membrane defines a first slit and a second slit through a thickness of the membrane, the first and second slits being linear and intersecting each other; and
first and second engagement tabs attached to an exterior surface of the tube proximate to a location of the membrane, the first and second engagement tabs radially extending from the tube in opposite directions along a tab axis that is orthogonal to the first slit, wherein the first and second engagement tabs are configured to be pulled away from each other to expand the tube along the tab axis and transition the membrane to a first open state that permits fluid flow through the membrane primarily within the first slit, wherein releasing the first and second engagement tabs causes the membrane to resiliently return to a closed state that restricts fluid flow through the membrane, and wherein the first and second engagement tabs are configured to be squeezed towards each other to compress the tube along the tab axis and transition the membrane to a second open state that permits fluid flow through the membrane primarily within the second slit.

19. The anti-free-flow valve of claim 18, wherein the membrane has a concave curved shape and the membrane is oriented relative to a direction of the fluid flow through the tube such that the concave curved shape funnels the fluid flow towards the first and second slits.

* * * * *